(12) United States Patent
Li et al.

(10) Patent No.: US 10,317,385 B2
(45) Date of Patent: Jun. 11, 2019

(54) CALIBRATION METHOD FOR WATER HARDNESS MEASUREMENT

(71) Applicant: Ecolab USA Inc., St. Paul, MN (US)

(72) Inventors: Hui Li, Bolingbrook, IL (US);
Alexandra Knoth, Aurora, IL (US);
Joe Schwartz, Aurora, IL (US);
Christopher Brant Wilson, Naperville, IL (US); Arthur Kahaian, Chicago, IL (US)

(73) Assignee: Ecolab USA Inc., St. Paul, MN (US)

( * ) Notice: Subject to any disclaimer, the term of this patent is extended or adjusted under 35 U.S.C. 154(b) by 307 days.

(21) Appl. No.: 15/200,728

(22) Filed: Jul. 1, 2016

(65) Prior Publication Data

US 2017/0003261 A1    Jan. 5, 2017

Related U.S. Application Data (60) Provisional application No. 62/187,559, filed on Jul. 1, 2015.

(51) Int. Cl.
*G01N 33/18* (2006.01)
*G01N 21/64* (2006.01)
(Continued)

(52) U.S. Cl.
CPC .......... *G01N 33/1853* (2013.01); *C09B 11/24* (2013.01); *C09B 67/0083* (2013.01);
(Continued)

(58) Field of Classification Search
CPC ... C09B 11/24; C09B 67/0083; G01N 21/274; G01N 21/278; G01N 21/6428;
(Continued)

(56) References Cited

U.S. PATENT DOCUMENTS 3,960,497 A    6/1976  Acord
4,355,072 A   10/1982  Mateika et al.
(Continued)

FOREIGN PATENT DOCUMENTS

KR    2008-0069209 A    7/2008
WO    2014/158403    * 10/2014

OTHER PUBLICATIONS

Biwersi et al., "Long-Wavelength Chloride-Sensitive Fluorescent Indicators," *Anal. Biochem.*, 219, pp. 139-143, 1994.
(Continued)

*Primary Examiner* — Maureen Wallenhorst
(74) *Attorney, Agent, or Firm* — Leydig Voit and Mayer, Ltd.

(57) ABSTRACT

Disclosed are methods that can be used to automatically calibrate a fluorescence-measuring instrument capable of continuously measuring the concentration of hardness in process water. The calibration method is used to compensate for drift of instrument and equipment, changes of operational conditions, and contamination of reagents and calibration standards. Calibration of the fluorescence-measuring instrument using the present calibration method improves both accuracy and repeatability for subsequent hardness concentration measurements.

20 Claims, 2 Drawing Sheets

(51) Int. Cl.
*G01N 21/27* (2006.01)
*C09B 11/24* (2006.01)
*C09B 67/44* (2006.01)

(52) U.S. Cl.
CPC ......... *G01N 21/274* (2013.01); *G01N 21/643* (2013.01); *G01N 21/645* (2013.01); *G01N 21/6428* (2013.01); *G01N 21/278* (2013.01); *G01N 33/1813* (2013.01); *G01N 2201/127* (2013.01)

(58) Field of Classification Search
CPC .............. G01N 21/643; G01N 21/645; G01N 2201/127; G01N 33/18; G01N 33/1813; G01N 33/1853; G01N 33/20
USPC .................. 436/8, 19, 73, 79, 164, 166, 172; 422/82.05, 82.08
See application file for complete search history.

(56) References Cited

U.S. PATENT DOCUMENTS

| | | | |
|---|---|---|---|
| 4,383,043 A | 5/1983 | Denney et al. | |
| 4,457,847 A | 7/1984 | Lorenc et al. | |
| 4,545,920 A | 10/1985 | Lorenc et al. | |
| 4,711,726 A | 12/1987 | Pierce et al. | |
| 4,999,305 A | 3/1991 | Wolcott et al. | |
| 5,041,386 A | 8/1991 | Pierce et al. | |
| 5,094,958 A | 3/1992 | Klainer et al. | |
| 5,173,434 A | 12/1992 | Morris et al. | |
| 5,302,253 A | 4/1994 | Lessard et al. | |
| 5,324,665 A | 6/1994 | Lessard | |
| 5,326,482 A | 7/1994 | Lessard et al. | |
| 5,384,050 A | 1/1995 | Kelley et al. | |
| 5,425,267 A | 6/1995 | Herrmann et al. | |
| 5,462,880 A | 10/1995 | Kane et al. | |
| 5,482,866 A | 1/1996 | Denton et al. | |
| 5,672,515 A | 9/1997 | Furlong | |
| 5,734,098 A | 3/1998 | Kraus et al. | |
| 5,736,405 A | 4/1998 | Alfano et al. | |
| 6,336,058 B1 | 1/2002 | Fowee | |
| 6,436,711 B1 | 8/2002 | Davis et al. | |
| 6,566,139 B2 | 5/2003 | Davis et al. | |
| 6,587,753 B2 | 7/2003 | Fowee | |
| 6,735,535 B1 | 5/2004 | Kagan et al. | |
| 6,790,664 B2 | 9/2004 | Bailey et al. | |
| 6,790,666 B2 | 9/2004 | Dang et al. | |
| 7,220,382 B2 | 5/2007 | Godfrey et al. | |
| 7,448,255 B2 | 11/2008 | Hoots et al. | |
| 7,951,298 B2 | 5/2011 | Hicks et al. | |
| 7,955,853 B2 | 6/2011 | Hicks et al. | |
| 8,068,033 B2 | 11/2011 | Blokker et al. | |
| 8,956,875 B2 | 2/2015 | Kahaian et al. | |
| 2003/0124730 A1 | 7/2003 | Bailey et al. | |
| 2003/0124731 A1 | 7/2003 | Dang et al. | |
| 2006/0246595 A1 | 11/2006 | Denney et al. | |
| 2007/0178595 A1 | 8/2007 | Raghuraman et al. | |
| 2007/0297945 A1* | 12/2007 | Leach ................... | G01N 21/31 422/82.05 |
| 2008/0179179 A1 | 7/2008 | Hicks et al. | |
| 2008/0202553 A1 | 8/2008 | Hicks et al. | |
| 2009/0177143 A1 | 7/2009 | Markle et al. | |
| 2010/0021958 A1 | 1/2010 | Reed et al. | |
| 2010/0108566 A1 | 5/2010 | Scattergood et al. | |
| 2012/0142113 A1 | 6/2012 | Banks et al. | |
| 2014/0273243 A1 | 9/2014 | Kahaian et al. | |
| 2015/0079688 A1 | 3/2015 | Kahaian et al. | |

OTHER PUBLICATIONS

Chalk et al., "Determination of Chloride by Flow Injection Spectrophotometry with Membrane Reagent Injection," *Analytica Chimica Acta*, 366, pp. 147-153, 1998.

Condias GmbH, "Condiapure Water Disinfection Bulletin," 2 pp., 2008.

De Armas et al., "Fluorimetric sequential injection determination of magnesium using 8-hydroxiquinoline-5-sulfonic acid in a micellar medium," *Talanta*, 52, pp. 77-82, 2000.

Dubois et al., "NeSSI™ (New Sampling/Sensor Initiative) Gen II Specification," *Center for Process Anal., Chem*, Univ. of Washington, pp. 1-53, Jun. 24, 2004.

Geddes, Chris, "Optical halide sensing using fluorescence quenching: theory, simulations and applications—a review," *Meas. Sci. and Tech.*, 12, pp. R53-R88, 2001.

Haines et al., "Errors in pH measurement with colorimetric indicators in low alkalinity waters," *Hydrobiologia*, 107, pp. 57-61, 1983.

Hoxter, Gunter, "Suggested Isosbestic Wavelength Calibration in Clinical Analyses," *Clin. Chem.*, 25(1), pp. 143-146, 1979.

Hupert et al., "Conductive diamond thin-films in electrochemistry," *Diamond and Related Materials*, 12, pp. 1940-1949, 2003.

KIPO, International Search Report in International Patent Application No. PCT/US2014/016076, 3 pp., dated May 8, 2014.

KIPO, Written Opinion in International Patent Application No. PCT/US2014/016076, 10 pp., dated May 8, 2014.

Koparal et al., "Electrochemical oxidation of sulfite ions in aqueous solutions," *Int. J. Environment and Pollution*, 21(6), pp. 579-587, 2004.

Lawrence et al., "Electrochemical Determination of Sulfide at Various Carbon Substrates: A Comparative Study," *Anal. Sci.*, 23, pp. 673-676, 2007.

Noiré et al., "A ferrous ion optical sensor based on fluorescence quenching," *Sensors and Actuators B*, 29, pp. 386-391, 1995.

Urbano et al., "Optical Sensor for Continuous Determination of Halides," *Anal. Chem.*, 56(3), pp. 427-429, Mar. 1984.

Waterston et al., "Electrochemical oxidation of sulfide ion at a boron-doped diamond anode," *J. of App. Electrochem.*, 37, pp. 367-373, 2007.

Zhelyaskov et al., "Analysis of nanoliter samples of electrolytes using a flow-through microfluorometer," *Kidney Int'l*, 57, pp. 1764-12769, 2000.

European Patent Office, International Search Report in International Patent Application No. PCT/US2016/040751, dated Sep. 15, 2016, 4 pp.

European Patent Office, Written Opinion in International Patent Application No. PCT/US2016/040751, dated Sep. 15, 2016, 1 p.

* cited by examiner

CALIBRATION METHOD FOR WATER HARDNESS MEASUREMENT

CROSS-REFERENCE TO RELATED APPLICATION

This patent application claims the benefit of U.S. Provisional Patent Application No. 62/187,559, filed Jul. 1, 2015, which is incorporated by reference in its entirety.

FIELD OF INVENTION

The invention is directed to calibration methods and standards for fluorometric analysis of low concentrations of metal ions in industrial water systems.

BACKGROUND OF THE INVENTION

Water hardness (i.e., magnesium and calcium) in an industrial water system can pose problems such as process inefficiencies and system shutdowns. Thus, the concentration of calcium and magnesium in an industrial water system should be carefully measured and monitored. Since hardness concentration can be quite low (e.g., ppb range), quantification of these metal cations requires a sensitive and precise method of measurement. If hardness is measured accurately, proper methods of hardness reduction can be selected (e.g., filtration, membrane purification, ion exchange, and chemical treatment), and appropriate chemical treatment dosages can be used to maintain low levels of hardness.

Spectroscopic analysis can be used to measure the concentration of calcium and magnesium in an industrial water system. However, accuracy of the method of analysis is dependent upon a number of factors. For example, operational variables such as flowrate, water pressure, and temperature can change between experimental runs, leading to inconsistent performance of instrumental pumps. In addition, the concentration of reagents can vary based on the commercial source, age, and manufacture of the reagent batch. Moreover, the background fluorescence of reagents employed can vary based on the impurity levels present in the batch. Variation of equipment components such as pumps, LEDs, and system electronics over time can erode analytical accuracy and reproducibility.

Calibration methods can be used to "zero" an instrument at the time of use to account for these variables. Preferably, the calibration method is easily executed, requires minimal human effort, and ensures instrumental accuracy and reproducibility. While many calibration methods exist, further improvement is always desirable.

BRIEF SUMMARY OF THE INVENTION

In an embodiment, the invention provides a method of calibrating a fluorescence-measuring instrument for soluble magnesium measurement. The method comprises measuring background fluorescence of a low calibration standard solution comprising soluble magnesium; combining a magnesium-reactant solution comprising an inert fluorescing agent and a magnesium coordinating fluorescing reagent with the low calibration standard solution, thereby forming a combined low calibration standard solution comprising the inert fluorescing agent and a coordinated magnesium compound; measuring fluorometric responses of the inert fluorescing agent and the coordinated magnesium compound in the combined low calibration standard solution; measuring fluorometric response of an inert fluorescing agent in a high calibration standard solution comprising soluble magnesium and inert fluorescing agent; combining a magnesium-reactant solution with the high calibration standard solution, thereby forming a combined high calibration standard solution comprising inert fluorescing agent and the coordinated magnesium compound; measuring fluorometric responses of the inert fluorescing agent and the coordinated magnesium compound in the combined high calibration standard solution; calibrating the fluorescence-measuring instrument based on the measured fluorometric responses and known concentration of soluble magnesium and inert fluorescing agent in the low calibration standard solution and in the high calibration standard solution.

In another embodiment, the invention provides a method of calibrating a fluorescence-measuring instrument for soluble magnesium and total hardness measurement. The method comprises measuring background fluorescence of a low calibration standard solution comprising soluble magnesium and soluble calcium; combining a magnesium-reactant solution comprising an inert fluorescing agent and a magnesium coordinating fluorescing reagent with the low calibration standard solution, thereby forming a combined low calibration standard solution comprising the inert fluorescing agent and a coordinated magnesium compound; measuring fluorometric responses of the inert fluorescing agent and the coordinated magnesium compound in the combined low calibration standard solution; combining the magnesium-reactant solution and a total hardness-reactant solution comprising a magnesium-containing reagent with the low calibration standard solution, thereby forming a calcium-displaced low calibration standard solution comprising the inert fluorescing agent and the coordinated magnesium compound; measuring fluorometric responses of the inert fluorescing agent and the coordinated magnesium compound in the calcium-displaced low calibration standard solution; measuring fluorometric response of the inert fluorescing agent in a high calibration standard solution comprising soluble magnesium, soluble calcium, and the inert fluorescing agent; combining the magnesium-reactant solution with the high calibration standard solution, thereby forming a combined high calibration standard solution comprising the inert fluorescing agent and the coordinated magnesium compound; measuring fluorometric responses of the inert fluorescing agent and the coordinated magnesium compound in the combined high calibration standard solution; combining the magnesium-reactant solution and the total hardness-reactant solution with the high calibration standard solution, thereby forming a calcium-displaced high calibration standard solution comprising the inert fluorescing agent and the coordinated magnesium compound; measuring fluorometric responses of the inert fluorescing agent and the coordinated magnesium compound in the calcium-displaced high calibration standard solution; calibrating the fluorescence-measuring instrument based on the measured fluorometric responses and known concentration of soluble magnesium, soluble calcium, and inert fluorescing agent in the low calibration standard solution and in the high calibration standard solution.

In another embodiment, the invention provides calibration standard solutions comprising (a) a first calibration standard solution comprising water, soluble magnesium at a concentration of from about 0 ppb to about 200 ppb, and soluble calcium at a concentration of from about 0 ppb to about 200 ppb; and (b) a second calibration standard solution comprising water, soluble magnesium at a concentration of from about 50 ppb to about 900 ppb, soluble calcium at a concentration of from about 50 ppb to about 900 ppb, and from about 1 ppb to about 20 ppb of an inert fluorescing agent capable of providing a fluorometric response to excitation light having a wavelength of from about 210 nm to about 830 nm.

DETAILED DESCRIPTION OF THE INVENTION

The following definitions are provided to determine how terms used in this application, and in particular, how the claims are to be construed. The organization of the definitions is for convenience only and is not intended to limit any of the definitions to any particular category.

As it pertains to this disclosure, "automatic," "automatically," and "automated" mean without human intervention or substantially without human intervention. For example, a process carried out automatically (i.e., an "automated process") would measure a variable and take action (e.g., change a pump speed, open or close a valve, increase heating or cooling, etc.) based on a comparison of the measured variable to a standard value (i.e., a setpoint) without a person having to do anything to make the action take place, outside of initially providing all necessary equipment, plumbing, wiring, power, programming, chemical ingredients, and so forth.

As it pertains to this disclosure, "as calcium carbonate" means that the particular concentration measurement (soluble magnesium, soluble calcium, or total hardness) is being reported "as calcium carbonate." Such a reporting method is commonly used in the field and makes uniform the measurement of each species or the total hardness, allowing for comparison across species.

As it pertains to this disclosure, "coordinate" or "coordinated" means a chemical connection of some sort that is sufficiently stable to allow the concentration and/or presence of a chemical species or compound to be measured by the known concentration of another chemical species or compound. For example, a fluorescing reagent may coordinate with a water soluble species in a ratio of one mole of water soluble species to one mole of fluorescing reagent, which would allow a fluorometric measurement of the water soluble species based on the known quantity of fluorescing reagent and/or experimental data related to the coordination of the water soluble species and the fluorescing reagent. Alternatively, the fluorescing reagent may coordinate with a water soluble species in a ratio of one mole of water soluble species to two moles of fluorescing reagent, which would allow a fluorometric measurement of the water soluble species based on the known quantity of fluorescing reagent and/or experimental data related to the coordination of the water soluble species and the fluorescing reagent (e.g., a calibration). Coordination of the known concentration of the fluorescing reagent allows for the quantification of the concentration of the water soluble species.

As it pertains to this disclosure, "correcting" or "correct" refers to making a change to a measured value based upon one or more variables. For example, a measured value may be knowingly affected by another measurable variable. With knowledge of the existence of the effect, one may correct for the known effect, thereby eliminating the effect in the first measured value. When dealing with fluorometry, effects related to temperature, dilution/concentration, and turbidity can introduce error into the raw fluorescence measurement and frequently require correction of the raw fluorescence measurement to reflect the effect.

As it pertains to this disclosure, "fluorescence-measuring instrument" refers to any instrument that can be used for fluorometric analysis. The instrument generally comprises a light source and a fluorescence detector (e.g., fluorometer) configured to fluorometrically detect fluorescence as known in the art. The instrument may also comprise a computer capable of performing calculations and storing data.

As it pertains to this disclosure, "inert fluorescing agent" refers to a fluorescing compound that does not react with other species (i.e., is inert), and fluoresces at a wavelength that does not interfere with the wavelengths of other present fluorescing species.

As it pertains to this disclosure, "magnesium coordinating fluorescing reagent" means a chemical compound that is capable of reacting with soluble magnesium to produce a coordinated magnesium compound. The coordinated magnesium compound may vary depending upon the particular magnesium coordinating fluorescing reagent utilized but will be capable of producing a fluorescent emission when coordinated with soluble magnesium and excited by light having a certain wavelength or range of wavelengths. Generally, when added to a water sample that contains soluble magnesium, a quantity of the magnesium coordinating fluorescing reagent coordinates (chemically attaches to soluble magnesium, thereby allowing for the measurement of soluble magnesium concentration via fluorescence) and a quantity may remain uncoordinated (e.g., the amount of the magnesium coordinating fluorescing agent that is residual or excess).

As it pertains to this disclosure, "magnesium-containing reagent" means a chemical compound that is at least partially made up of magnesium and that reacts with a known species that may be present in a substance. For example, in certain embodiments of the methods disclosed herein, the magnesium-containing reagent reacts with soluble calcium that is present in an aliquot of water, thereby displacing the soluble calcium with soluble magnesium.

The invention is generally directed to calibration methods and standards that can be used to calibrate a fluorescence instrument used to measure soluble magnesium and/or calcium concentrations (i.e., hardness) in aqueous media. In certain embodiments, the present disclosure is directed to automated calibration methods of monitoring hardness in water entering or re-entering an industrial process. An accurate calibration method is needed to ensure accuracy of the measurement of low concentrations of soluble magnesium and soluble calcium in industrial water. The present method can be used to automatically "zero" a fluorescence-measuring instrument by calibrating the measurement of soluble magnesium and total hardness (i.e., total soluble magnesium and soluble calcium). In particular, calibration standard solutions comprising known amounts of soluble magnesium, soluble calcium, and an inert fluorescing agent are measured using the fluorescence-measuring instrument. In certain embodiments, the concentration of soluble magnesium in a calibration standard solution is quantified using a magnesium coordinating fluorescing reagent to coordinate soluble magnesium and measuring the fluorescence of the coordinated magnesium compound. In certain embodiments, the total hardness in a calibration standard solution is quantified by displacement of soluble calcium in the standard solution using a magnesium-containing reagent, and then coordinating the soluble magnesium with a magnesium coordinating fluorescing reagent and measuring the fluorescence of the coordinated magnesium compound. The measurements are used to generate linear or essentially linear calibration curves, which are used to automatically calibrate the fluorescence-measuring instrument.

In an embodiment, the invention provides a method of calibrating a fluorescence-measuring instrument for soluble magnesium measurement. The method comprises measuring background fluorescence of a low calibration standard solution comprising soluble magnesium; combining a magnesium-reactant solution comprising an inert fluorescing agent and a magnesium coordinating fluorescing reagent with the low calibration standard solution, thereby forming a combined low calibration standard solution comprising the inert fluorescing agent and a coordinated magnesium compound; measuring fluorometric responses of the inert fluorescing agent and the coordinated magnesium compound in the combined low calibration standard solution; measuring fluorometric response of an inert fluorescing agent in a high calibration standard solution comprising soluble magnesium and inert fluorescing agent; combining a magnesium-reactant solution with the high calibration standard solution, thereby forming a combined high calibration standard solution comprising inert fluorescing agent and the coordinated magnesium compound; measuring fluorometric responses of the inert fluorescing agent and the coordinated magnesium compound in the combined high calibration standard solution; calibrating the fluorescence-measuring instrument based on the measured fluorometric responses and known concentration of soluble magnesium and inert fluorescing agent in the low calibration standard solution and in the high calibration standard solution.

In another embodiment, the invention provides a method of calibrating a fluorescence-measuring instrument for soluble magnesium measurement. The method comprises introducing a low calibration standard solution comprising soluble magnesium into the fluorescence-measuring instrument; measuring background fluorescence of the low calibration standard solution; combining a magnesium-reactant solution comprising an inert fluorescing agent and a magnesium coordinating fluorescing reagent with the low calibration standard solution, thereby forming a combined low calibration standard solution comprising the inert fluorescing agent and a coordinated magnesium compound; measuring fluorometric responses of the inert fluorescing agent and the coordinated magnesium compound in the combined low calibration standard solution; introducing a high calibration standard solution comprising soluble magnesium and the inert fluorescing agent into the fluorescence-measuring instrument; measuring fluorometric response of the inert fluorescing agent in the high calibration standard solution; combining a magnesium-reactant solution with the high calibration standard solution, thereby forming a combined high calibration standard solution comprising the inert fluorescing agent and the coordinated magnesium compound; measuring fluorometric responses of the inert fluorescing agent and the coordinated magnesium compound in the combined high calibration standard solution; calibrating the fluorescence-measuring instrument based on the measured fluorometric responses and known concentration of soluble magnesium and inert fluorescing agent in the low calibration standard solution and in the high calibration standard solution.

In another embodiment, the invention provides a method of calibrating a fluorescence-measuring instrument for soluble magnesium and total hardness measurement. The method comprises measuring background fluorescence of a low calibration standard solution comprising soluble magnesium and soluble calcium; combining a magnesium-reactant solution comprising an inert fluorescing agent and a magnesium coordinating fluorescing reagent with the low calibration standard solution, thereby forming a combined low calibration standard solution comprising the inert fluorescing agent and a coordinated magnesium compound; measuring fluorometric responses of the inert fluorescing agent and the coordinated magnesium compound in the combined low calibration standard solution; combining the magnesium-reactant solution and a total hardness-reactant solution comprising a magnesium-containing reagent with the low calibration standard solution, thereby forming a calcium-displaced low calibration standard solution comprising the inert fluorescing agent and the coordinated magnesium compound; measuring fluorometric responses of the inert fluorescing agent and the coordinated magnesium compound in the calcium-displaced low calibration standard solution; measuring fluorometric response of the inert fluorescing agent in a high calibration standard solution comprising soluble magnesium, soluble calcium, and the inert fluorescing agent; combining the magnesium-reactant solution with the high calibration standard solution, thereby forming a combined high calibration standard solution comprising the inert fluorescing agent and the coordinated magnesium compound; measuring fluorometric responses of the inert fluorescing agent and the coordinated magnesium compound in the combined high calibration standard solution; combining the magnesium-reactant solution and the total hardness-reactant solution with the high calibration standard solution, thereby forming a calcium-displaced high calibration standard solution comprising the inert fluorescing agent and the coordinated magnesium compound; measuring fluorometric responses of the inert fluorescing agent and the coordinated magnesium compound in the calcium-displaced high calibration standard solution; calibrating the fluorescence-measuring instrument based on the measured fluorometric responses and known concentration of soluble magnesium, soluble calcium, and inert fluorescing agent in the low calibration standard solution and in the high calibration standard solution.

In another embodiment, the invention provides a method of calibrating a fluorescence-measuring instrument for soluble magnesium and total hardness measurement. The method comprises introducing a low calibration standard solution comprising soluble magnesium and soluble calcium into the fluorescence-measuring instrument; measuring background fluorescence of the low calibration standard solution; combining a magnesium-reactant solution comprising an inert fluorescing agent and a magnesium coordinating fluorescing reagent with the low calibration standard solution, thereby forming a combined low calibration standard solution comprising the inert fluorescing agent and a coordinated magnesium compound; measuring the fluorometric responses of the inert fluorescing agent and the coordinated magnesium compound in the combined low calibration standard solution; combining the magnesium-reactant solution and a total hardness-reactant solution comprising a magnesium-containing reagent with the low calibration standard solution, thereby forming a calcium-displaced low calibration standard solution comprising the inert fluorescing agent and the coordinated magnesium compound; measuring the fluorometric responses of the inert fluorescing agent and the coordinated magnesium compound in the calcium-displaced low calibration standard solution; introducing a high calibration standard solution comprising soluble magnesium, soluble calcium, and the inert fluorescing agent into the fluorescence-measuring instrument; measuring the fluorometric response of the inert fluorescing agent in the high calibration standard solution; combining the magnesium-reactant solution with the high calibration standard solution, thereby forming a combined high calibration standard solution comprising the inert fluorescing agent and the coordinated magnesium compound; measuring the fluorometric responses of the inert fluorescing agent and the coordinated magnesium compound in the combined high calibration standard solution; combining the magnesium-reactant solution and the total hardness-reactant solution with the high calibration standard solution, thereby forming a calcium-displaced high calibration standard solution comprising the inert fluorescing agent and the coordinated magnesium compound; measuring the fluorometric responses of the inert fluorescing agent and the coordinated magnesium compound in the calcium-displaced high calibration standard solution; calibrating the fluorescence-measuring instrument based on the measured fluorometric responses and known concentration of soluble magnesium, soluble calcium, and inert fluorescing agent in the low calibration standard solution and in the high calibration standard solution.

In certain preferred embodiments, the fluorescence-measuring instrument is automatically calibrated.

In certain preferred embodiments, a calibration curve is plotted based on the measured fluorometric responses and known concentration of soluble magnesium, soluble calcium, total hardness, and/or inert fluorescing agent in the low calibration standard solution and in the high calibration standard solution, and is used to calibrate the fluorescence-measuring instrument. In certain preferred embodiments, the fluorescence-measuring instrument automatically calculates the y-intercept and slope of the calibration curve.

In certain embodiments, a controller is a component of the fluorescence-measuring instrument, or a controller is connected to the fluorescence-measuring instrument. In certain preferred embodiments, the controller has a storage means for storing information, including concentrations and measured fluorometric responses. In certain preferred embodiments, the y-intercept and the slope of the calibration curve are stored in a storage device of the controller (e.g., computer). In certain preferred embodiments, the fluorescence-measuring instrument comprises a driver board that stores the equation and variables of the calibration curve. In certain preferred embodiments, an equation of the calibration curve is stored in a storage device of the controller (e.g., computer) and the equation is used to automatically calibrate the fluorescence-measuring instrument.

In certain preferred embodiments, the y-intercept and the slope of the calibration curve are used to calculate the concentration of soluble magnesium, soluble calcium, and/or total hardness in a water sample (e.g., industrial water sample). The fluorescence signal of the water sample is measured using the fluorescence-measuring instrument, and converted to concentration (e.g., soluble magnesium or total hardness) by a driver board in the fluorescence-measuring instrument using the stored y-intercept and slope of the calibration curve. In certain embodiments, the accuracy of the calibration method can be determined by measuring the concentration of soluble magnesium, soluble calcium, and/or total hardness in a known water sample (e.g., industrial water sample), and comparing the measured concentration with the known concentration of soluble magnesium, soluble calcium, and/or total hardness.

In certain preferred embodiments, the fluorescence-measuring instrument is flushed with the low calibration standard solution prior to calibration of the instrument. In certain preferred embodiments, the fluorescence-measuring instrument is flushed with the appropriate calibration standard solution (i.e., low calibration standard solution and high calibration standard solution) prior to each measuring step. In certain preferred embodiments, the fluorescence-measuring instrument is automatically flushed with the appropriate calibration standard solution (i.e., low calibration standard solution and high calibration standard solution) prior to each measuring step. In certain preferred embodiments, the fluorescence-measuring instrument is flushed for at least about 5 seconds with the appropriate calibration standard solution.

The above methods are directed to the calibration of a fluorescence instrument used to measure soluble magnesium and/or total hardness concentration. The calibration methods of the present invention can be used to calibrate a fluorescence-measuring instrument used to measure soluble magnesium and/or total hardness concentration by any suitable method. For example, the concentration of soluble magnesium and/or total hardness in water can be determined as disclosed in U.S. Pat. No. 8,956,875, which is hereby incorporated by reference.

The present calibration method comprises measuring a known amount of soluble magnesium and/or total hardness in a calibration standard solution. The concentration of soluble magnesium in a calibration standard solution (e.g., low calibration standard solution and high calibration standard solution) is measured by combining a suitable magnesium coordinating fluorescing reagent with a calibration standard solution comprising soluble magnesium. The magnesium coordinating fluorescing reagent coordinates with soluble magnesium in the calibration standard solution, forming a coordinated magnesium compound. The concentration of soluble magnesium in the calibration standard solution is determined by measuring the fluorescence of the coordinated magnesium compound.

The total hardness (i.e., total soluble magnesium and soluble calcium) of a calibration standard solution is measured using the concept of calcium displacement. In particular, soluble calcium in a calibration standard solution is displaced by combining a magnesium-containing reagent with the calibration standard solution. The magnesium-containing reagent displaces the dissolved calcium in the calibration standard solution with soluble magnesium at a known ratio, typically one mole of soluble magnesium for each mole of soluble calcium. The displacement allows for the determination of the total hardness concentration that represents all the soluble magnesium and soluble calcium in the calibration standard. As in the case of the soluble magnesium measurement, a suitable magnesium coordinating fluorescing reagent can coordinate with the soluble magnesium to form a coordinated magnesium compound. The total hardness concentration in the calibration standard is determined by measuring the fluorescence of the coordinated magnesium compound. In certain embodiments, the soluble calcium concentration is then determined by subtracting a first measured magnesium concentration (representing only soluble magnesium) from the measured total hardness concentration.

In certain preferred embodiments, the present calibration method provides individual 2-point calibration curves for soluble magnesium, total hardness, and inert fluorescing agent. For each calibration, the two calibration standard solutions (e.g., low calibration standard solution and high calibration standard solution) having known concentrations of analyte are analyzed to provide linear or essentially linear calibration curves.

When the calibration method is used to calibrate a fluorescence-measuring instrument, the calibration curves are generated by the computer of the fluorescence-measuring instrument by correlating the measured fluorometric responses with the known concentration of analyte (e.g., soluble magnesium, soluble calcium, and soluble inert fluorescing agent), thereby creating a calibration curve for soluble magnesium, inert fluorescing agent, and/or total hardness. In certain embodiments, the calibration curves are straight or essentially straight lines. In certain preferred embodiments, the fluorescence-measuring instrument can automatically determine the equation of the calibration curve or line, including the slope and y-intercept. In certain preferred embodiments, the calibration curve for the inert fluorescing agent does not go through the number zero. In certain preferred embodiments, the calibration curve equation is stored in the instrument. The stored calibration curve can be used to calculate the concentration of soluble magnesium, soluble calcium, and/or total hardness of a water sample.

Dilution of the calibration standard solution occurs when the standard solution is combined with the magnesium-reactant solution and/or total hardness-reactant solution. A dilution factor must be taken into account when the fluorescence-measuring instrument calculates the concentration of soluble magnesium and/or total hardness from fluorescence values. In certain preferred embodiments, the inert fluorescing agent is used to calculate the dilution factor, correcting the error associated with dilution resulting from the addition of aqueous reagents. In certain preferred embodiments, the soluble magnesium concentration determined via fluorescence measurement of the coordinated magnesium compound can be corrected using the inert fluorescing agent to account for one or more of the following: variation in mixing ratio, variation in background effects, and variation in temperature, thereby allowing for the calculation of an adjusted soluble magnesium concentration in the water. In certain embodiments, the inert fluorescing agent is used to determine the proper mixing ratio of reagents (e.g., magnesium coordinating fluorescing reagent and/or magnesium-containing reagent) to calibration standard solution.

In certain preferred embodiments, the inert fluorescing agent is present in the magnesium-reactant solution and the total hardness-reactant solution to monitor the level of the magnesium-coordinating fluorescing reagent and/or the magnesium-containing reagent. However, in certain embodiments, the magnesium-reactant solution and/or total hardness-reactant solution does not comprise inert fluorescing agent.

For the calibration method, the magnesium coordinating fluorescing reagent is combined with the calibration standard solution (e.g., low calibration standard solution or high calibration standard solution) at a particular mixing ratio (volume/volume). In certain embodiments, the mixing ratio of the calibration standard solution to the magnesium coordinating fluorescing reagent is about 100 to 1 or less, by volume. In certain preferred embodiments, the mixing ratio of the low calibration standard solution to the magnesium coordinating fluorescing reagent is about 50 to 1 or less, by volume. In a certain preferred embodiment, the mixing ratio of the low calibration standard solution to the magnesium coordinating fluorescing reagent is about 49 to 1, by volume.

For calibration of total hardness of the present invention, the magnesium coordinating fluorescing agent, magnesium-containing reagent, and calibration standard solution (e.g., low calibration standard solution or high calibration standard solution) are combined at a particular mixing ratio (volume/volume). In certain embodiments, the mixing ratio of the calibration standard solution to the magnesium coordinating fluorescing reagent to the magnesium-containing reagent is about 100 to 1 to 1 or less, by volume. In certain preferred embodiments, the mixing ratio of the low calibration standard solution to the magnesium coordinating fluorescing reagent to the magnesium-containing reagent is about 50 to 1 to 1 or less, by volume. In a certain preferred embodiment, the mixing ratio of the low calibration standard solution to the magnesium coordinating fluorescing reagent to the magnesium-containing reagent is about 48 to 1 to 1, by volume.

The low calibration standard solution and high calibration standard solution can comprise soluble magnesium and soluble calcium at any suitable concentration. The present methods are typically used to calibration an instrument for measuring low concentrations of soluble magnesium and/or soluble calcium. In certain embodiments, the concentration of soluble magnesium and soluble calcium may be from about 0 ppb to about 200 ppb. However, more accurate results are obtained when the concentration of soluble magnesium and soluble calcium are greater than zero (e.g., 50 ppb to 200 ppb). In certain preferred embodiments, the low calibration standard solution comprises soluble magnesium at a concentration of from about 0 ppb to about 200 ppb. Thus, in certain preferred embodiments, the low calibration standard solution comprises soluble magnesium at a concentration of from about 0 ppb to about 200 ppb, from about 0 ppb to about 150 ppb, from about 0 ppb to about 100 ppb, from about 0 ppb to about 200 ppb, from about 0 ppb to about 150 ppb, from about 0.01 ppb to about 200 ppb, from about 0.01 ppb to about 150 ppb, from about 0.01 ppb to about 100 ppb, from about 0.01 ppb to about 50 ppb, from about 50 ppb to about 200 ppb, from about 50 ppb to about 150 ppb, from about 50 ppb to about 100 ppb, or from about 100 ppb to about 200 ppb. In certain preferred embodiments, the low calibration standard solution further comprises soluble calcium at a concentration of from about 0 ppb to about 200 ppb, from about 0 ppb to about 150 ppb, from about 0 ppb to about 100 ppb, from about 0 ppb to about 200 ppb, or from about 0 ppb to about 200 ppb, 0.01 ppb to about 200 ppb, from about 0.01 ppb to about 150 ppb, from about 0.01 ppb to about 100 ppb, from about 0.01 ppb to about 50 ppb, from about 50 ppb to about 200 ppb, from about 50 ppb to about 150 ppb, from about 50 ppb to about 100 ppb, or from about 100 ppb to about 200 ppb. The concentration of soluble magnesium and soluble calcium in the low calibration standard solution can be the same or different. In certain preferred embodiments, the concentration of soluble magnesium and the concentration of soluble calcium are substantially the same on a weight-to-weight basis.

In certain preferred embodiments, the high calibration standard solution comprises soluble magnesium at a concentration of from about 50 ppb to about 900 ppb. Thus, in certain preferred embodiments, the high calibration standard solution comprises soluble magnesium at a concentration of from about 50 ppb to about 900 ppb, from about 50 ppb to about 850 ppb, from about 50 ppb to about 800 ppb, from about 50 ppb to about 750 ppb, from about 50 ppb to about 700 ppb, from about 100 ppb to about 900 ppb, from about 200 ppb to about 900 ppb, from about 300 ppb to about 900 ppb, from about 400 ppb to about 900 ppb, from about 500 ppb to about 900 ppb, from about 600 ppb to about 900 ppb, from about 700 ppb to about 900 ppb, from about 200 ppb to 900 ppb, from about 200 ppb to about 850 ppb, or from about 200 ppb to about 800 ppb. In certain preferred embodiments, the high calibration standard solution further comprises soluble calcium at a concentration of from about 50 ppb to about 900 ppb, from about 50 ppb to about 850 ppb, from about 50 ppb to about 800 ppb, from about 50 ppb to about 750 ppb, from about 50 ppb to about 700 ppb, from about 100 ppb to about 900 ppb, from about 200 ppb to about 900 ppb, from about 300 ppb to about 900 ppb, from about 400 ppb to about 900 ppb, from about 500 ppb to about 900 ppb, from about 600 ppb to about 900 ppb, from about 700 ppb to about 900 ppb, from about 200 ppb to about 900 ppb, from about 200 ppb to about 850 ppb, or from about 200 ppb to about 800 ppb. The concentration of soluble magnesium and soluble calcium in the high calibration standard solution can be the same or different. In certain preferred embodiments, the concentration of soluble magnesium and the concentration of soluble calcium are substantially the same on a weight-to-weight basis.

In certain preferred embodiments, the two calibration standard solutions have a concentration difference of from about 50 ppb to about 850 ppb, i.e., the concentration of soluble magnesium and/or soluble calcium in the low calibration standard solution subtracted from the concentration of soluble magnesium and/or soluble calcium in the high calibration standard solution is from about 50 ppb to about 850 ppb.

As discussed above, the high calibration standard solution comprises an inert fluorescing agent capable of providing a fluorometric response. The inert fluorescing agent can be any suitable fluorescent compound. In certain embodiments, the inert fluorescing agent is selected from the group consisting of a derivative of Rhodamine, a derivative of fluorescein, and combinations thereof. In certain preferred embodiments, the inert fluorescing agent is Rhodamine WT. In certain preferred embodiments, the inert fluorescing agent is chosen so that its fluorescence wavelength does not interfere with the fluorescence wavelength of the magnesium coordinating fluorescing agent.

The high calibration standard solution can comprise inert fluorescing agent at any suitable concentration. Since the instrumentation is used to measure low concentrations of soluble magnesium and soluble calcium, the high calibration standard solution typically comprises inert fluorescing agent at a concentration of from about 1 ppb to about 20 ppb. Thus, in certain preferred embodiments, the high calibration solution comprises inert fluorescing agent at a concentration of from about 1 ppb to about 20 ppb, from about 1 ppb to about 15 ppb, from about 1 ppb to about 10 ppb, from about 1 ppb to about 9 ppb, from about 1 ppb to about 8 ppb, from about 1 ppb to about 7 ppb, from about 1 ppb to about 6 ppb, from about 1 ppb to about 5 ppb, from about 2 ppb to about 20 ppb, from about 2 ppb to about 15 ppb, from about 2 ppb to about 10 ppb, from about 2 ppb to about 8 ppb, from about 2 ppb to about 6 ppb, from about 5 ppb to about 20 ppb, from about 5 ppb to about 15 ppb, from about 5 ppb to about 10 ppb, from about 10 ppb to about 20 ppb, or from about 10 ppb to about 15 ppb.

In certain embodiments, the inert fluorescing agent is capable of providing a fluorometric response to excitation light having a wavelength of from about 210 nm to about 830 nm, from about 210 nm to about 800 nm, from about 210 nm to about 700 nm, from about 210 nm to about 600 nm, from about 210 nm to about 500 nm, from about 300 nm to about 830 nm, from about 400 nm to about 830 nm, from about 500 nm to about 830 nm, from about 600 nm to about 830 nm, from about 450 nm to about 750 nm, or from about 620 nm to about 700 nm.

The magnesium coordinating fluorescing reagent can be any suitable fluorescent compound. In certain embodiments, the magnesium coordinating fluorescing reagent is selected from the group consisting of a water soluble, aromatic, ortho hydroxyl substituted azo dye, a water soluble, fused-ring heterocycle; and combinations thereof. In certain embodiments, where the magnesium coordinating fluorescing reagent comprises at least one water soluble, aromatic, ortho hydroxyl substituted azo dye, it is selected from the group consisting of Plasmocorinth B, Eriochrome Black T, Calmagite, 8-hydroxyquinolone-5-sulfonic acid, and combinations thereof. In certain preferred embodiments, the magnesium coordinating fluorescing reagent is 8-hydroxyquinolone-5-sulfonic acid ("HQS"). In certain preferred embodiments, the magnesium coordinating fluorescing reagent is added to the calibration standard solution at a concentration of from about 0.01 ppm to about 1000 ppm.

The magnesium-containing reagent can be any suitable magnesium-containing compound. In certain embodiments, the magnesium-containing reagent comprises a magnesium-containing multidentate chelant. In certain embodiments, the magnesium-containing reagent comprises an organic diamine. In certain preferred embodiments, the magnesium-containing multidentate chelant comprises disodium magnesium 1,2-diaminecyclohexyl-N,N,N',N' tetraacetate. In certain preferred embodiments, the magnesium-containing reagent is magnesium (1,2,-diaminocyclohexanetetraacetic acid disodium salt). In certain preferred embodiments, the magnesium-containing reagent is combined with the calibration standard solution as solution having a concentration of from about 0.01 ppm to about 1000 ppm. In certain embodiments, the soluble calcium is displaced with soluble magnesium by overdosing the magnesium-containing reagent (e.g., using a large excess of reagent with regard to hardness).

The inert fluorescing agent used in the high calibration standard solution can be the same or different from the inert fluorescing agent used in the magnesium-reactant solution and the total hardness-reactant solution. In certain preferred embodiments, the high calibration standard solution, magnesium-reactant solution, and the total hardness solution comprise the same inert fluorescing agent. In certain embodiments, the high calibration standard solution, magnesium-reactant solution, and the total hardness-reactant solution each comprise a different inert fluorescing agent. In certain embodiments, the magnesium-reactant solution and the total hardness solution comprise the same inert fluorescing agent. In certain embodiments, the magnesium-reactant solution and the total hardness-reactant solution each comprise a different inert fluorescing agent. In certain embodiments, the high calibration standard solution and the magnesium-reactant solution comprise the same inert fluorescing agent. In certain embodiments, the high calibration standard solution and the total hardness-reactant solution comprise the same inert fluorescing agent.

In certain embodiments, a water soluble non-coordinating base capable of buffering an aqueous solution to a pH of from about 8 to about 12 can be combined with the solutions of the present invention. In certain embodiments, a low calibration standard solution comprises a water soluble non-coordinating base capable of buffering an aqueous solution to a pH of from about 8 to about 12. In certain embodiments, a high calibration standard solution comprises a water soluble non-coordinating base capable of buffering an aqueous solution to a pH of from about 8 to about 12. In certain embodiments, a magnesium-reactant solution comprises a water soluble non-coordinating base capable of buffering an aqueous solution to a pH of from about 8 to about 12. In certain embodiments, a total hardness-reactant solution comprises a water soluble non-coordinating base capable of buffering an aqueous solution to a pH of from about 8 to about 12. In certain preferred embodiments, the water soluble, non-coordinating base is a sterically-hindered organic base. In certain preferred embodiments, the water soluble, non-coordinating base is 1,4-diazabicyclo[2.2.2]octane.

The methods of the present invention can be conducted manually or automatically. In certain preferred embodiments, the calibration method is conducted automatically. In other words, the each step of the method is carried out automatically or nearly automatically, i.e., without or with only minimal human intervention. The only human intervention required is the minimal act of replacing depleted ingredients, including but not limited to the following ingredients or any of their precursors or sub-ingredients: the magnesium coordinating fluorescing reagent; the magnesium-containing reagent; the inert fluorescing agent; or any calibration standard solution.

The methods of the present invention are generally conducted using a fluorescence-measuring instrument comprising a fluorometer comprising a light source and a fluorescence detector configured to detect fluorescence as known in the art. The fluorescence-measuring instrument may comprise any suitable fluorometer. In certain embodiments, the present methods are carried out using a light source capable of shining light at a particular wavelength. In certain embodiments, the fluorescence detector is capable of measuring the intensity of emitted fluorescence of an analyte.

The fluorometer may be chosen from a filter fluorometer or a spectrofluorometer. In a certain preferred embodiment, the fluorometric techniques are carried out using an excitation light source capable of shining light at a particular wavelength or wavelength range, such as an arc lamp (e.g., mercury, xenon, tungsten-halogen, or xenon-mercury arc lamp), a laser, or a light emitting diode (LED). In certain preferred embodiments, the excitation light source is a light emitting diode (LED). In certain embodiments, the fluorescence detector is capable of filtering excitation wavelength(s) of light from emission wavelength(s) of light using, e.g., a monochromatic filter, dichroic filter, or long pass filter.

In certain embodiments, the fluorescence-measuring instrument comprises a fluorometer and a controller (e.g., computer) configured to measure a fluorescent signal in a sample. In certain embodiments, the known concentration of analyte (e.g., soluble magnesium, soluble calcium, and/or total hardness) is entered into the controller manually. In other embodiments, the known concentration of analyte is automatically measured by the fluorescence-measuring instrument. When a computer is employed, the computer comprises a program capable of automatically graphing the fluorometric response (e.g., intensity of fluorescent signal) of an analyte vs. the known concentration of the analyte to create a calibration curve. In certain preferred embodiments, the calibration curve and its line equation are stored in the computer's memory (e.g., RAM). The y-intercept and the slope of the stored calibration curve can be used to calculate the concentration of analyte in a water sample. In certain embodiments, the execution of various machine-implemented processes and steps described herein occurs via the computerized execution of processor-executable instructions stored on a non-transitory computer-readable medium (e.g., RAM, ROM, PROM, volatile, nonvolatile, or other electronic memory mechanism) by one or more corresponding processor(s).

For automated embodiments, the various components are in communication with a processing unit that has been programmed to logically control the various active components according to parameters that may be set by the user or determined in some other fashion. For example, in certain preferred embodiments, a controller transmits a pre-programmed sequence to the fluorescence-measuring instrument and each step of the calibration method is carried out automatically. In certain embodiments, the processing unit may be shared with other control systems employed with the industrial process. In certain embodiments, the processing unit comprises a programmable logic controller ("PLC").

For example, an automated monitoring system may be wired and plumbed so as to perform any sampling and measurement without human intervention, outputting a measured value either constantly or at intervals without a user having to initiate such sampling or measurement. For certain measurements, combining of reagents and solvents can be performed automatically using automated controls. In certain embodiments, a powered sensor detects a fluorescence or absorbance at a particular wavelength. The sensor sends a first electrical signal to a control system which in turn may send a second electrical signal to a powered and controlled operation (e.g., a pump or a valve) based on the first electrical signal and user input in the form of a control program, at least one setpoint, and optionally fine tuning. The control system is programmed and may be fine tuned to control around a particular setpoint, for example, based on measured hardness. The control program may control several variables, including flow rates and the reagents involved with calibrating hardness. Non-limiting actions that may be taken by the control program include changing the rate or amount of reagent, and/or acting to dilute reagents by switching on water pumps.

In certain preferred embodiments, the fluorescence-measuring instrument comprises a driver board capable of configuring optical parameters of the fluorometer. In certain preferred embodiments, the fluorescence-measuring instrument comprises an inert fluorescing agent board and a hardness board. The hardness board configures the fluorometer for fluorescence measurement of a coordinated magnesium compound or magnesium coordinating fluorescing agent. The inert fluorescing agent board and the hardness board may have the same or different optical parameters. In certain embodiments, the fluorometer is configured by the inert fluorescing agent board to emit light at a wavelength of from about 310 nm to about 400 nm and to detect fluorescence at a wavelength of from about 550 nm to about 650 nm. In certain preferred embodiments, the fluorometer is configured by the inert fluorescing agent board to emit light at a wavelength of from about 325 nm to about 375 nm and to detect fluorescence at a wavelength of from about 560 nm to about 620 nm. In certain preferred embodiments, the fluorometer is configured by the hardness driver to emit light at a wavelength of from about 475 nm to about 550 nm and detect fluorescence at a wavelength of from about 450 nm to about 500 nm. In certain preferred embodiments, the fluorometer is configured by the hardness driver to emit light at a wavelength of from about 450 nm to about 575 nm and detect fluorescence at a wavelength of from about 425 nm to about 525 nm.

Figure 1:
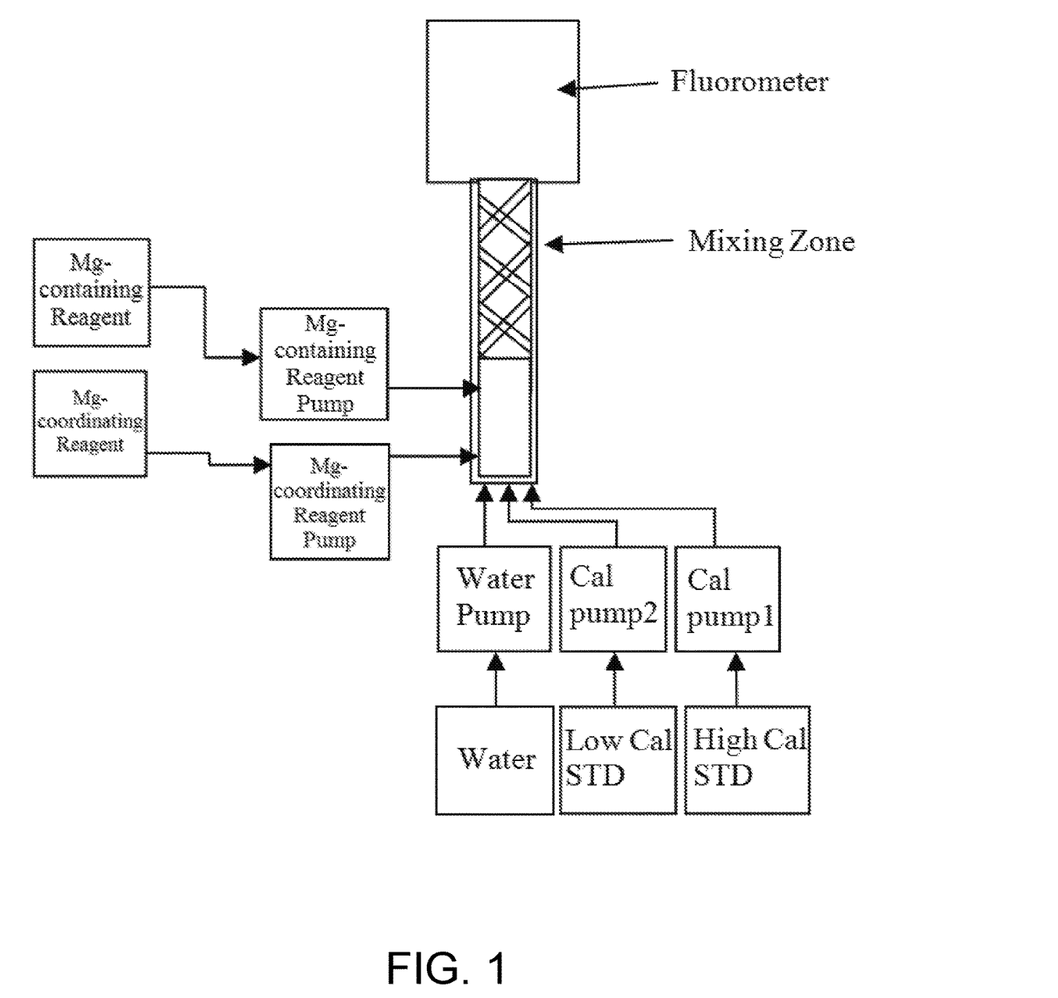
FIG. 1 displays a diagram for calibration of a fluorescence-measuring instrument in accordance with an embodiment of the invention.

In certain embodiments, the fluorescence-measuring instrument is as shown in FIG. 1. In such embodiments, the fluorescence-measuring instrument comprises a fluorometer, individual containers for reagent and calibration standard solutions, individual pumps for reagents and calibration standard solutions, and a mixing zone where reagent and calibration standard solution are allowed to mix.

In certain embodiments, the fluorescence-measuring instrument comprises a fluorometer, analyzer equipment, and a controller. The analyzer equipment may include reagent pumps, water pumps, standard solution pumps (e.g., low calibration standard solution and high calibration standard solution pump), containers, and a mixing chamber. In certain preferred embodiments, the reagents and standard solutions are stored in containers (e.g., bags), each connected to a separate pump via a tube. A reagent (e.g., magnesium coordinating fluorescing reagent or magnesium-containing reagent) is injected into a stream of standard solution (e.g., low calibration standard solution or high calibration standard solution) by pumping the reagent from the reagent container into a stream of standard solution using a reagent pump. The mixture may be mixed in a mixing chamber. In certain preferred embodiments, the fluid mixture is then pushed by the water pump into the fluorometer through a static mixer, which helps to create a homogenous solution.

In certain embodiments, the amount or quantity of the standard solution (e.g., low calibration standard solution or high calibration standard solution) is determined via mechanical methods (e.g., weight/mass measurements and/or calculations, flow measurements and/or calculations, volume measurements and/or calculations, etc., which may be determined using, e.g., one or more metering pumps, scales, load cells, rotameters, etc.), fluorometry, light absorbance, pressure compensation, flow compensation, and combinations thereof.

The solutions and reagents of the present invention can be combined using any suitable technique. In certain preferred embodiments, a reagent (e.g., magnesium coordinating fluorescing reagent or magnesium-containing compound) is combined with a calibration standard solution by injecting the reagent into a flow of the calibration standard solution. In certain preferred embodiments, the combining of reagents and calibration standard solutions is conducted automatically.

In certain preferred embodiments, a calibration method of the present invention is conducted on the fluorescence-measuring instrument periodically. In certain preferred embodiments, the calibration method is conducted at the time the user changes or refills the reagent batch (e.g., magnesium coordinating fluorescing reagent and magnesium-containing reagent). In certain preferred embodiments, the calibration method is conducted upon installation of a new reagent batch because regents inherently have variability with respect to contaminant content from one package to the next.

In another embodiment, the invention provides a calibration standard solution suitable for use in a fluorometric hardness measurement procedure. The calibration standard solution is an aqueous liquid comprising a known concentration of soluble magnesium and soluble calcium and is suitable for use in a fluorometric hardness calibration procedure. The calibration standard solution comprises water, soluble magnesium at a concentration of from about 0 ppb to about 900 ppb, and soluble calcium at a concentration of from about 0 ppb to about 900 ppb.

The calibration standard solution comprises soluble magnesium at a concentration of from about 0 ppb to about 900 ppb, and soluble calcium at a concentration of from about 0 ppb to about 900 ppb. Thus, in certain embodiments, the calibration standard solution comprises soluble magnesium at a concentration of from about 0 ppb to about 900 ppb, from about 0 ppb to about 800 ppb, from about 0 ppb to about 700 ppb, from about 0 ppb to about 600 ppb, from about 0 ppb to about 500 ppb, from about 0 ppb to about 400 ppb, from about 0 ppb to about 300 ppb, from about 0 ppb to about 200 ppb, 0.01 ppb to about 900 ppb, from about 0.01 ppb to about 800 ppb, from about 0.01 ppb to about 700 ppb, from about 0.01 ppb to about 600 ppb, from about 0.01 ppb to about 500 ppb, from about 0.01 ppb to about 400 ppb, from about 0.01 ppb to about 300 ppb, from about 0.01 ppb to about 250 ppb, from about 100 ppb to about 900 ppb, from about 200 ppb to about 900 ppb, from about 300 ppb to about 900 ppb, from about 400 ppb to about 900 ppb, from about 500 ppb to about 900 ppb, or from about 600 ppb to about 900 ppb. In certain embodiments, the calibration standard solution further comprises soluble calcium at a concentration of from about 0 ppb to about 900 ppb, from about 0 ppb to about 800 ppb, from about 0 ppb to about 700 ppb, from about 0 ppb to about 600 ppb, from about 0 ppb to about 500 ppb, from about 0 ppb to about 400 ppb, from about 0 ppb to about 300 ppb, from about 0 ppb to about 200 ppb, 0.01 ppb to about 900 ppb, from about 0.01 ppb to about 800 ppb, from about 0.01 ppb to about 700 ppb, from about 0.01 ppb to about 600 ppb, from about 0.01 ppb to about 500 ppb, from about 0.01 ppb to about 400 ppb, from about 0.01 ppb to about 300 ppb, from about 0.01 ppb to about 250 ppb, from about 100 ppb to about 900 ppb, from about 200 ppb to about 900 ppb, from about 300 ppb to about 900 ppb, from about 400 ppb to about 900 ppb, from about 500 ppb to about 900 ppb, or from about 600 ppb to about 900 ppb. In certain embodiments, the concentration of soluble magnesium and the concentration of soluble calcium are substantially the same on a weight-to-weight basis.

In another embodiment, the invention provides calibration standard solutions comprising (a) a first calibration standard solution comprising water, soluble magnesium at a concentration of from about 0 ppb to about 200 ppb, and soluble calcium at a concentration of from about 0 ppb to about 200 ppb; and (b) a second calibration standard solution comprising water, soluble magnesium at a concentration of from about 50 ppb to about 900 ppb, soluble calcium at a concentration of from about 50 ppb to about 900 ppb, and from about 1 ppb to about 20 ppb of an inert fluorescing agent capable of providing a fluorometric response to excitation light having a wavelength of from about 210 nm to about 830 nm.

In certain preferred embodiments, the first calibration standard solution comprises soluble magnesium at a concentration of from about 0 ppb to about 200 ppb, and soluble calcium at a concentration of from about 0 ppb to about 200 ppb. Thus, in certain embodiments, the first calibration standard solution comprises soluble magnesium at a concentration of from about 0 ppb to about 200 ppb, from about 0 ppb to about 150 ppb, from about 0 ppb to about 100 ppb, from about 50 ppb to about 200 ppb, from about 50 ppb to about 150 ppb, from about 50 ppb to about 100 ppb, from about 100 ppb to about 200 ppb, or from about 100 ppb to about 150 ppb. In certain preferred embodiments, the first calibration standard solution further comprises soluble calcium at a concentration of from about 0 ppb to about 200 ppb, from about 0 ppb to about 150 ppb, from about 0 ppb to about 100 ppb, from about 50 ppb to about 200 ppb, from about 50 ppb to about 150 ppb, from about 50 ppb to about 100 ppb, from about 100 ppb to about 200 ppb, or from about 150 ppb to about 200 ppb. The concentration of soluble magnesium and soluble calcium in the first calibration standard solution can be substantially the same or different. In certain preferred embodiments, the concentration of soluble magnesium and the concentration of soluble calcium are substantially the same on a weight-to-weight basis.

In certain embodiments, the second calibration standard solution comprises soluble magnesium at a concentration of from about 50 ppb to about 900 ppb, and soluble calcium at a concentration of from about 50 ppb to about 900 ppb. Thus, in certain embodiments, the second calibration standard solution comprises soluble magnesium at a concentration of from about 50 ppb to about 900 ppb, from about 50 ppb to about 850 ppb, from about 50 ppb to about 800 ppb, from about 50 ppb to about 750 ppb, from about 50 ppb to about 700 ppb, from about 100 ppb to about 900 ppb, from about 200 ppb to about 900 ppb, from about 300 ppb to about 900 ppb, from about 400 ppb to about 900 ppb, from about 500 ppb to about 900 ppb, from about 600 ppb to about 900 ppb, from about 700 ppb to about 900 ppb, from about 200 ppb to 900 ppb, from about 200 ppb to about 850 ppb, or from about 200 ppb to about 800 ppb. In certain embodiments, the second calibration standard solution further comprises soluble calcium at a concentration of from about 50 ppb to about 900 ppb, from about 50 ppb to about 850 ppb, from about 50 ppb to about 800 ppb, from about 50 ppb to about 750 ppb, from about 50 ppb to about 700 ppb, from about 100 ppb to about 900 ppb, from about 200 ppb to about 900 ppb, from about 300 ppb to about 900 ppb, from about 400 ppb to about 900 ppb, from about 500 ppb to about 900 ppb, from about 600 ppb to about 900 ppb, from about 700 ppb to about 900 ppb, from about 200 ppb to 900 ppb, from about 200 ppb to about 850 ppb, or from about 200 ppb to about 800 ppb. The concentration of soluble magnesium and soluble calcium in the first calibration standard solution can be substantially the same or different. In certain preferred embodiments, the concentration of soluble magnesium and the concentration of soluble calcium are substantially the same on a weight-to-weight basis.

In certain embodiments, the first calibration standard solution comprises a water soluble non-coordinating base capable of buffering an aqueous solution to a pH of from about 8 to about 12. In certain embodiments, the second calibration standard solution comprises a water soluble non-coordinating base capable of buffering an aqueous solution to a pH of from about 8 to about 12. In certain embodiments, the first calibration standard solution and second calibration standard solution comprise a water soluble non-coordinating base capable of buffering an aqueous solution to a pH of from about 8 to about 12. In certain preferred embodiments, the water soluble, non-coordinating base is a sterically-hindered organic base. In certain preferred embodiments, the water soluble, non-coordinating base is 1,4-diazabicyclo[2.2.2]octane.

The calibration standard solutions of the present disclosure can be formed using any suitable magnesium salt or calcium salt. In certain embodiments, a calibration standard solution is formed by combining a water-soluble magnesium and/or a water-soluble calcium salt with water. In certain embodiments, the calibration standard solution is formed by combining with water a magnesium salt selected from the group consisting of magnesium chloride, magnesium acetate, magnesium bromide, magnesium iodide, magnesium nitrate, magnesium chlorate, and magnesium sulfate. In certain embodiments, the calibration standard solution is further formed by combining with water comprising a magnesium salt a calcium salt selected from the group consisting of calcium chloride, calcium acetate, calcium bromide, calcium iodide, calcium chlorate, and calcium nitrate. In certain preferred embodiments, the calibration standard solution is formed by combining magnesium chloride and/or calcium chloride with water.

The second calibration standard solution comprises an inert fluorescing agent capable of providing a fluorometric response. The inert fluorescing agent can be any suitable fluorescent compound. In certain embodiments, the inert fluorescing agent is selected from the group consisting of a derivative of Rhodamine, a derivative of fluorescein, and combinations thereof. In certain preferred embodiments, the inert fluorescing agent is Rhodamine WT. In certain embodiments, the second calibration standard solution comprises inert fluorescing agent at a concentration of from about 1 ppb to about 20 ppb. Thus, in certain embodiments, the second calibration solution comprises inert fluorescing agent at a concentration of from about 1 ppb to about 20 ppb, from about 1 ppb to about 15 ppb, from about 1 ppb to about 10 ppb, from about 1 ppb to about 5 ppb, from about 2 ppb to about 20 ppb, from about 2 ppb to about 15 ppb, from about 2 ppb to about 10 ppb, from about 2 ppb to about 5 ppb, from about 5 ppb to about 20 ppb, from about 5 ppb to about 15 ppb, or from about 5 ppb to about 10 ppb.

As discussed above, the inert fluorescing agent is capable of providing a fluorometric response to excitation light having a wavelength of from about 210 nm to about 830 nm. Thus, in certain embodiments, the inert fluorescing agent is capable of providing a fluorometric response to excitation light having a wavelength of from about 210 nm to about 830 nm, from about 210 nm to about 700 nm, from about 210 nm to about 600 nm, from about 210 nm to about 500 nm, from about 210 nm to about 400 nm, from about 300 nm to about 830 nm, from about 400 nm to about 830 nm, from about 450 nm to about 750 nm, from about 500 nm to about 830 nm, from about 300 nm to about 700 nm, or from about 300 nm to about 600 nm.

In certain embodiments, the present invention is used to calibrate a fluorescence-measuring instrument used to analyze water comprising soluble magnesium and/or soluble calcium at a concentration of 3000 ppb or less, measured as calcium carbonate.

In certain preferred embodiments, the hardness concentration is calculated as parts per billion calcium carbonate.

In certain preferred embodiments, the present invention is used to automatically calibrate a fluorescence-measuring instrument capable of continuously measuring the concentration of hardness (e.g., soluble magnesium, soluble calcium, and/or total hardness) in industrial water. In certain preferred embodiments, the present invention is used to adjust the response of the fluorescence detector in a hardness-measurement method.

In certain preferred embodiments, the fluorescence-measuring instrument comprising a fluorometer, analyzer equipment, and a controller is about 2 ft×2 ft×2 ft or less. In certain preferred embodiments, the fluorescence-measuring instrument comprising a fluorometer, analyzer equipment, and a controller is about 1.5 ft×1.5 ft×1.5 ft or less. In certain preferred embodiments, the fluorescence-measuring instrument comprising a fluorometer, analyzer equipment, and a controller is about 1 ft×1 ft×1 ft or less.

In certain embodiments, a method of the present invention is used to determine if a reagent should be replaced. In certain embodiments, a method of the present invention is used to determine if a component of the fluorescence-measuring instrument should be replaced or repaired (e.g., sensor, light source, or pump).

The following examples further illustrate the invention but, of course, should not be construed as in any way limiting its scope.

Example 1

This Example illustrates a method of calibration of a fluorescence-measuring instrument for measuring soluble magnesium and total hardness in accordance with an embodiment of the invention.

All hardness concentrations are calculated as parts per billion calcium carbonate. A fluorescence-measuring instrument was auto-calibrated using a low calibration standard, a high calibration standard, a magnesium-reactant solution comprising a magnesium-coordinating fluorescing reagent, and a total hardness-reactant solution comprising a magnesium-containing reagent. The low calibration standard comprised 0 ppb Rhodamine WT, 100 ppb soluble magnesium, and 100 ppb soluble calcium. The high calibration standard comprised 8 ppb Rhodamine WT, 800 ppb soluble magnesium, and 800 ppb soluble calcium. The magnesium-reactant solution comprised 8-hydroxyquinoline-5-sulfonic acid (HQS), 1,4-diazabicyclo[2.2.2]octane (DABCO), and Rhodamine WT. The total hardness-reactant solution comprised magnesium (1,2-diaminocyclohexanetetraacetic acid disodium salt) ($Na_2MgCDTA$), DABCO, and Rhodamine WT. HQS and DABCO were purchased from Aldrich. Rhodamine WT was purchased from Turner Scientific. $Na_2MgCDTA$ was purchased from Hach.

Preparation of Calibration Standard Solutions. A 100 ppm solution of soluble calcium was prepared by dissolving $CaCl_2.2H_2O$ (1.470 g, 10 mmol) in 1.0 liter of deionized water, and further diluting a 100 mL aliquot of the solution with deionized water until the total volume was 1.0 liter. A 100 ppm solution of soluble magnesium was prepared by dissolving $MgCl_2.6H_2O$ (2.033 g, 10 mmol) in 1.0 liter of deionized water, and further diluting a 100 mL aliquot of the solution with deionized water until the total volume was 1.0 liter. The low calibration standard solution was prepared by adding 1.0 mL of 100 ppm soluble calcium solution and 1.0 mL of 100 ppm soluble magnesium solution to a volumetric flask and diluting the solution with deionized water until the total volume was 1.0 liter.

A 200 ppb Rhodamine WT solution was prepared by adding 1 mL of Rhodamine WT (20% aq. soln.) to a 1.0 liter volumetric flask and adding deionized water until the total volume was 1.0 liter. A 1.0 mL aliquot of the solution was diluted with deionized water until the total volume was 1.0 liter. The high calibration standard was prepared by adding 8.0 mL of 100 ppm soluble calcium solution, 8.0 mL of 100 ppm soluble magnesium solution, and 40 mL of 200 ppb Rhodamine WT solution to a volumetric flask and diluting with deionized water until the total volume was 1.0 liter. The 100 ppm soluble calcium solution and 100 ppm soluble magnesium solution was prepared from the same stock solutions as described above.

Preparation of the Reagents. The magnesium-reactant solution was prepared by combining 8-hydroxyquinoline-5-sulfonic acid (HQS, 750 mg, 3.3 mmol), DABCO (15.0 g, 133 mmol), and an aqueous Rhodamine WT solution (1 mL of 200 ppm solution) in a 1 liter volumetric flask and diluting with deionized water until the total volume was 1.0 liter. The total hardness-reactant solution was prepared by dissolving $Na_2MgCDTA$ (15.0 g, 36.2 mmol) and DABCO (15.0 g, 133 mmol) in deionized water. The mixture was filtered, added to a 1 liter volumetric flask, and charged with an aqueous solution of Rhodamine WT (1 mL of 200 ppm solution). The mixture was diluted with deionized water until the total volume was 1 liter.

Auto-calibration Method. The fluorescence-measuring instrument was injected with the low calibration standard for about 2 minutes. After flushing the instrument, a fluorescence measurement was performed to determine the background fluorescence. Next, magnesium-reactant solution was injected into the stream of the low calibration standard for 30 seconds at a volumetric ratio of 1:49 (magnesium-reactant solution to low calibration standard). The fluorescence of both Rhodamine WT and coordinated magnesium was measured to detect the concentration of soluble magnesium. Next, the low calibration standard was injected for 2 minutes to flush residual magnesium-coordinating fluorescing reagent from the instrument. The total hardness-reactant solution and magnesium-reactant solution was injected into the stream of the low calibration standard for 30 seconds at a volumetric ratio of 1:1:48 (total hardness-reactant solution to magnesium-reactant solution to low calibration standard). The injection of total hardness-reactant solution, magnesium-reactant solution, and low calibration standard was halted and the mixture was allowed to dwell for 5 minutes. After 5 minutes, the fluorescence of both Rhodamine WT and coordinated magnesium compound (representing the total hardness) was measured.

Next, the fluorescence-measuring instrument was injected with the high calibration standard for about 2 minutes. After flushing the instrument, the fluorescence of Rhodamine WT in the high calibration standard was measured. Next, magnesium-reactant solution was injected into the stream of the high calibration standard for 30 seconds at a volumetric ratio of 1:49 (magnesium-reactant solution to high calibration standard). The fluorescence of both Rhodamine WT and coordinated magnesium was measured to detect the concentration of soluble magnesium. Next, the high calibration standard was injected for 2 minutes to flush residual magnesium-coordinating fluorescing reagent from the instrument. The total hardness-reactant solution and magnesium-reactant solution was injected into the stream of the high calibration standard for 30 seconds at a volumetric ratio of 1:1:48 (total hardness-reactant solution to magnesium-reactant solution to high calibration standard). The injection of total hardness-reactant solution, magnesium-reactant solution, and high calibration standard was halted and the mixture was allowed to dwell for 5 minutes. After 5 minutes, the fluorescence of both Rhodamine WT and coordinated magnesium compound (representing the total hardness) was measured.

The fluorescence-measuring instrument automatically generated and stored calibration curve equations for Rhodamine WT, magnesium hardness, and total hardness (i.e., soluble magnesium and soluble calcium) based on the known concentrations and measured fluorescence. The calibration curve equations can be used by the fluorescence-measuring instrument to calculate the concentration of soluble magnesium, soluble calcium, and total hardness of a sample. The calibration curve equation for Rhodamine WT can be used by the instrument to determine the dilution factor, which is used during the calibration as well as for subsequent hardness measurements.

Example 2

This Example illustrates utility of the auto-calibration method of Example 1 for measuring soluble magnesium and total hardness in a sample.

The auto-calibration method of Example 1 was validated by measuring soluble magnesium, soluble calcium, and total hardness in two samples containing known amounts of soluble magnesium and soluble calcium. A sample comprising 200 ppb soluble calcium and 200 ppb soluble magnesium, and a sample comprising 500 ppb soluble calcium and 500 ppb soluble magnesium were analyzed using the same fluorescence-measuring instrument auto-calibrated in Example 1. The results of the experiments were plotted as shown in FIG. 2.

Figure 2:
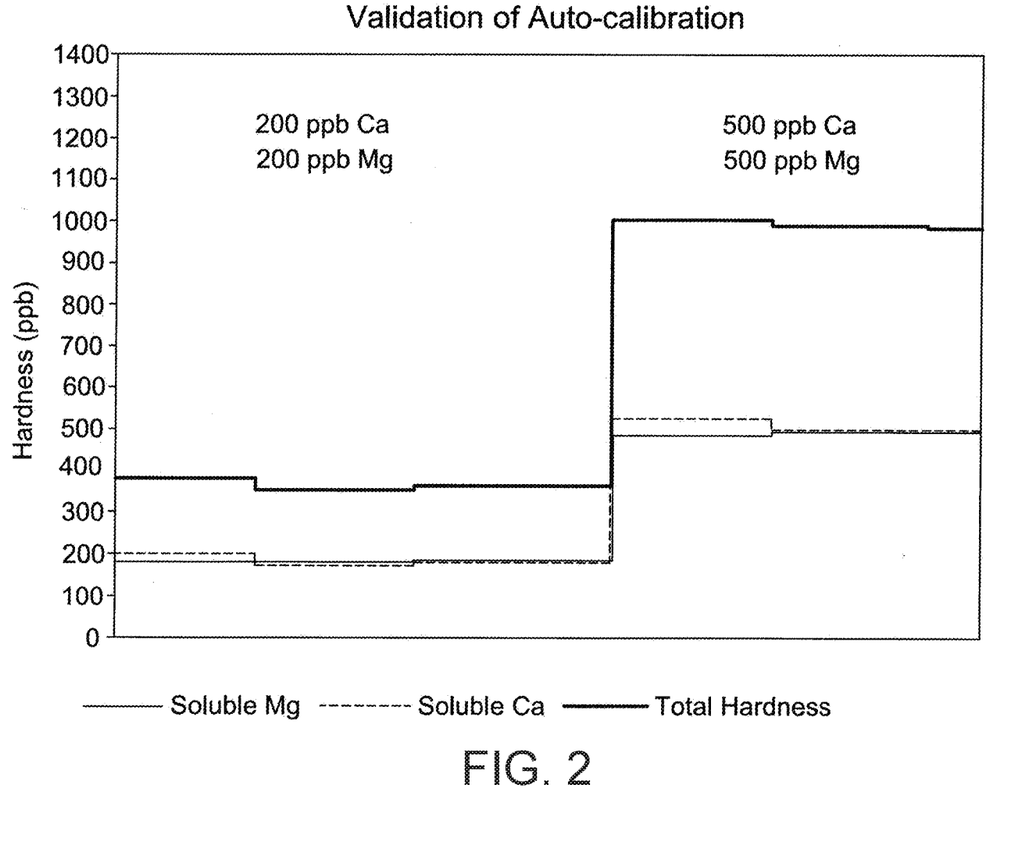
FIG. 2 displays a graph illustrating the accuracy of a calibration method in accordance with an embodiment of the invention.

As shown in FIG. 2, the auto-calibrated fluorescence-measuring instrument yielded concentration readings that were close to the known concentration of the samples.

This Example demonstrates that a fluorescence-measuring instrument calibrated according to a method of an embodiment of the invention can be used to accurately measure low concentrations of soluble magnesium, soluble calcium, and total hardness.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of calibrating a fluorescence-measuring instrument for soluble magnesium, the method comprising:
    measuring background fluorescence of a low calibration standard solution comprising soluble magnesium at a known concentration;
    combining a magnesium-reactant solution comprising an inert fluorescing agent at a known concentration and a magnesium coordinating fluorescing reagent with the low calibration standard solution, thereby forming a combined low calibration standard solution comprising the inert fluorescing agent and a coordinated magnesium compound;
    measuring fluorometric responses of the inert fluorescing agent and the coordinated magnesium compound in the combined low calibration standard solution;
    measuring fluorometric response of an inert fluorescing agent in a high calibration standard solution comprising both soluble magnesium and inert fluorescing agent at known concentrations;
    combining the magnesium-reactant solution with the high calibration standard solution, thereby forming a combined high calibration standard solution comprising inert fluorescing agent and a coordinated magnesium compound;
    measuring fluorometric responses of the inert fluorescing agent and the coordinated magnesium compound in the combined high calibration standard solution; and
    calibrating the fluorescence-measuring instrument based on the measured fluorometric responses and the known concentrations of soluble magnesium and inert fluorescing agent in the low calibration standard solution and in the high calibration standard solution.

2. The method of claim 1, wherein the fluorescence-measuring instrument is calibrated by plotting a calibration curve for magnesium and inert fluorescing agent based on the measured fluorometric responses and known concentrations of soluble magnesium and inert fluorescing agent in the low calibration standard solution and in the high calibration standard solution and the calibration curve is used to calibrate the fluorescence-measuring instrument.

3. The method of claim 2, wherein an equation of the calibration curve is stored by a controller and the equation is used to automatically calibrate the fluorescence-measuring instrument.

4. The method of claim 1, wherein the fluorescence-measuring instrument is flushed with the low calibration standard solution or the high calibration standard solution prior to each measuring step.

5. The method of claim 1, wherein the low calibration standard solution comprises soluble magnesium at a concentration of from about 50 ppb to about 200 ppb, and the high calibration standard solution comprises soluble magnesium at a concentration of from about 300 ppb to about 900 ppb, and the inert fluorescing agent at a concentration of about 1 ppb to about 20 ppb.

6. The method of claim 1, wherein the inert fluorescing agent is Rhodamine WT.

7. The method of claim 1, wherein the magnesium coordinating fluorescing reagent is 8-hydroxyquinoline-5-sulfonic acid.

8. The method of claim 1, wherein the low and high calibration standard solutions have a soluble magnesium concentration difference of from about 50 ppb to about 850 ppb.

9. The method of claim 1, wherein the low calibration standard solution has a concentration of soluble magnesium of from about 50 ppb to about 200 ppb.

10. A method of calibrating a fluorescence-measuring instrument for soluble magnesium and total hardness, the method comprising:

measuring background fluorescence of a low calibration standard solution comprising soluble magnesium and soluble calcium each at known concentrations;

combining a magnesium-reactant solution comprising an inert fluorescing agent at a known concentration and a magnesium coordinating fluorescing reagent with the low calibration standard solution, thereby forming a combined low calibration standard solution comprising the inert fluorescing agent and a coordinated magnesium compound;

measuring fluorometric responses of the inert fluorescing agent and the coordinated magnesium compound in the combined low calibration standard solution;

combining the magnesium-reactant solution and a total hardness-reactant solution comprising a magnesium-containing reagent with the low calibration standard solution, thereby forming a calcium-displaced low calibration standard solution comprising the inert fluorescing agent and the coordinated magnesium compound;

measuring fluorometric responses of the inert fluorescing agent and the coordinated magnesium compound in the calcium-displaced low calibration standard solution in order to measure total hardness;

measuring fluorometric response of an inert fluorescing agent in a high calibration standard solution comprising soluble magnesium, soluble calcium, and the inert fluorescing agent, each at known concentrations;

combining the magnesium-reactant solution with the high calibration standard solution, thereby forming a combined high calibration standard solution comprising the inert fluorescing agent and a coordinated magnesium compound;

measuring fluorometric responses of the inert fluorescing agent and the coordinated magnesium compound in the combined high calibration standard solution;

combining the magnesium-reactant solution and the total hardness-reactant solution with the high calibration standard solution, thereby forming a calcium-displaced high calibration standard solution comprising the inert fluorescing agent and the coordinated magnesium compound;

measuring fluorometric responses of the inert fluorescing agent and the coordinated magnesium compound in the calcium-displaced high calibration standard solution in order to measure total hardness; and calibrating the fluorescence-measuring instrument based on the measured fluorometric responses, the known concentrations of soluble magnesium and inert fluorescing agent, and the measurements of total hardness in the low calibration standard solution and in the high calibration standard solution.

11. The method of claim 10, wherein the fluorescence-measuring instrument is calibrated by plotting a calibration curve for soluble magnesium, total hardness, and the inert fluorescing agent based on the measured fluorometric responses and known concentrations of soluble magnesium, soluble calcium, and inert fluorescing agent in each of the low calibration standard solution and in the high calibration standard solution.

12. The method of claim 11, wherein an equation of the calibration curve is stored by a controller and the equation is used to automatically calibrate the fluorescence-measuring instrument.

13. The method of claim 10, wherein the fluorescence-measuring instrument is flushed with the low calibration standard solution or the high calibration standard solution prior to each measuring step.

14. The method of claim 10, wherein the low calibration standard solution comprises soluble magnesium at a concentration of from about 50 ppb to about 200 ppb and soluble calcium at a concentration of from about 50 ppb to about 200 ppb; and the high calibration standard solution comprises soluble magnesium at a concentration of from about 300 ppb to about 900 ppb, soluble calcium at a concentration of from about 300 ppb to about 900 ppb, and the inert fluorescing agent at a concentration of about 1 ppb to about 20 ppb.

15. The method of claim 10, wherein the inert fluorescing agent is Rhodamine WT.

16. The method of claim 10, wherein the magnesium coordinating fluorescing reagent is 8-hydroxyquinoline-5-sulfonic acid.

17. The method of claim 10, wherein the magnesium-containing reagent is magnesium (1,2-diaminocyclohexanetetraacetic acid disodium salt).

18. The method of claim 10, wherein the low and high calibration standard solutions have a soluble magnesium concentration difference of from about 50 ppb to about 850 ppb.

19. The method of claim 10, wherein the low and high calibration standard solutions have a soluble calcium concentration difference of from about 50 ppb to about 850 ppb.

20. The method of claim 10, wherein the low calibration standard solution has a concentration of soluble magnesium of from about 50 ppb to about 200 ppb.

* * * * *